United States Patent
Yalamareddy et al.

(10) Patent No.: US 9,957,279 B2
(45) Date of Patent: May 1, 2018

(54) PROCESS FOR THE PREPARATION OF INTERMEDIATES USEFUL IN THE PREPARATION OF HEPATITIS C VIRUS (HCV) INHIBITORS

(71) Applicant: Laurus Labs Private Limited, Hyderabad (IN)

(72) Inventors: Kirshna R. Yalamareddy, Plano, TX (US); Clifton Leigh, Somerville, MA (US); Sankar Subramanian, Auburndale, MA (US); Stephen Mccarron, Lexington, MA (US); Omar Depaolis, Allston, MA (US); Lyndon Marble, Brookline, NH (US)

(73) Assignee: LAURUS LABS LIMITED, Hyderabad (IN)

( * ) Notice: Subject to any disclaimer, the term of this patent is extended or adjusted under 35 U.S.C. 154(b) by 0 days. days.

(21) Appl. No.: 15/583,722

(22) Filed: May 1, 2017

(65) Prior Publication Data
US 2017/0320885 A1    Nov. 9, 2017

Related U.S. Application Data

(60) Provisional application No. 62/332,193, filed on May 5, 2016.

(51) Int. Cl.
*C07D 491/048*    (2006.01)
*C07C 255/54*    (2006.01)
*C07D 311/78*    (2006.01)

(52) U.S. Cl.
CPC ........ *C07D 491/048* (2013.01); *C07C 255/54* (2013.01); *C07D 311/78* (2013.01)

(58) Field of Classification Search
CPC .................................................. C07D 491/048
USPC .......................................................... 549/384
See application file for complete search history.

(56) References Cited

U.S. PATENT DOCUMENTS

| | | | |
|---|---|---|---|
| 6,387,926 B1 | 5/2002 | Bhide et al. |
| 8,575,135 B2 | 11/2013 | Bacon et al. |
| 8,921,341 B2 | 12/2014 | Bacon et al. |
| 8,940,718 B2 | 1/2015 | Bacon et al. |
| 2009/0047249 A1 | 2/2009 | Graupe et al. |
| 2013/0156732 A1 | 6/2013 | Bacon et al. |
| 2015/0191437 A1 | 7/2015 | Shekhar et al. |
| 2016/0115175 A1 | 4/2016 | Bacon et al. |

FOREIGN PATENT DOCUMENTS

WO    WO-2015/191437 A1    12/2015

OTHER PUBLICATIONS

Woo, L.W. et al., "Steroidal and Nonsteroidal Sulfamates as Potent Inhibitors of Steroid Sulfatase," J. Med. Chem., 1998, 41(7), pp. 1068-1083.
International Search Report for PCT/IB/52527 dated Oct. 13, 2017.

*Primary Examiner* — Taofiq A Solola
(74) *Attorney, Agent, or Firm* — Blank Rome LLP

(57) ABSTRACT

The present invention generally relates to a process for preparation of 9-halo-3-(2-haloacetyl)-10,11-dihydro-5H-dibenzo[c,g]chromen-8(9H)-one of Formula I, which is an intermediate in the preparation of Hepatitis C Virus (HCV) inhibitors.

32 Claims, No Drawings

PROCESS FOR THE PREPARATION OF INTERMEDIATES USEFUL IN THE PREPARATION OF HEPATITIS C VIRUS (HCV) INHIBITORS

CROSS-REFERENCE TO RELATED APPLICATIONS

This application is related to and claims the benefit of the filing date of U.S. Provisional Patent Application No. 62/332,193, filed May 5, 2016, entitled "Process for the Preparation of Intermediates Useful in the Preparation of Hepatitis C Virus (HCV) Inhibitors," the content of which is incorporated by reference herein.

BACKGROUND OF THE INVENTION

Field of the Invention

The present invention generally relates to a process for the preparation of 9-halo-3-(2-haloacetyl)-10,11-dihydro-5H-dibenzo[c,g]chromen-8(9H)-one of Formula I, which is an intermediate used in the preparation of Hepatitis C Virus (HCV) inhibitors, particularly used in the preparation of Velpatasvir of Formula A.

Description of the Related Art

The compound, 9-halo-3-(2-haloacetyl)-10,11-dihydro-5H-dibenzo[c,g]chromen-8(9H)-one of Formula I is used as an intermediate in the preparation of Velpatasvir of Formula A. The structural identification of 9-halo-3-(2-haloacetyl)-10,11-dihydro-5H-dibenzo[c,g]chromen-8(9H)-one of Formula I, wherein 'X' represents a halogen; is represented as follows:

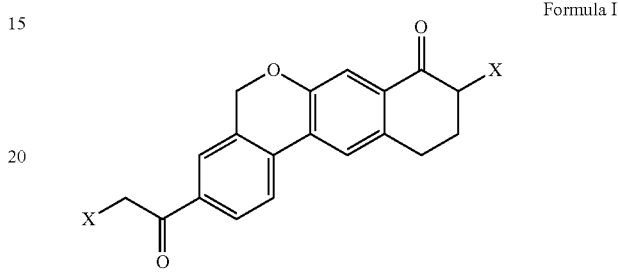

Formula I

Velpatasvir is chemically known as methyl {(2S)-1-[(2S,5S)-2-(9-{2-[(2S,4S)-1-{(2R)-2-[(methoxycarbonyl)amino-]-2-phenylacetyl}-4-(methoxymethyl)pyrrolidin-2-yl]-1H-imidazol-5-yl}-1,11-dihydroisochromeno[4',3':6,7]naphtho[1,2-d] imidazol-2-yl)-5-methylpyrroli-din-1-yl]-3-methyl-1-oxobutan-2-yl}carbamate; represented by the following structure:

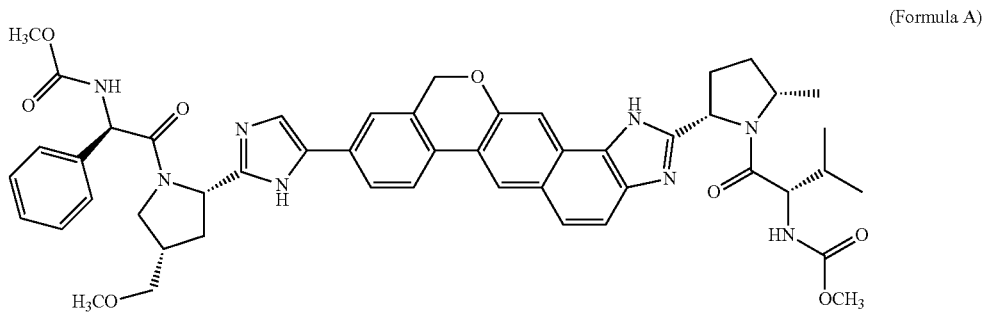

(Formula A)

Velpatasvir

Velpatasvir is an investigational pan-genotypic NS5A inhibitor and is presently under clinical trials in combination with nucleotide analog polymerase inhibitor sofosbuvir (SOF), approved as Sovaldi®, for the treatment of chronic genotype 1-6 hepatitis C virus HCV infection.

U.S. Pat. No. 8,940,718 ("the '718 patent"), U.S. Pat. No. 8,575,135 ("the '135 patent") and U.S. Pat. No. 8,921,341 ("the '341 patent") discloses new HCV therapeutic agents such as Velpatasvir of Formula A and its intermediate of Formula I, and processes for their preparation. The process disclosed for preparation of compound of Formula I in the '718 patent is schematically represented as follows:

Scheme-1

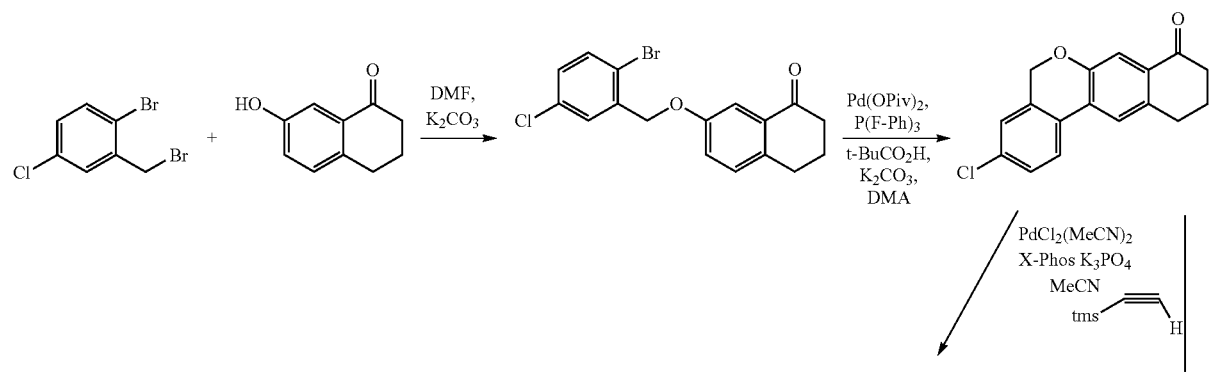

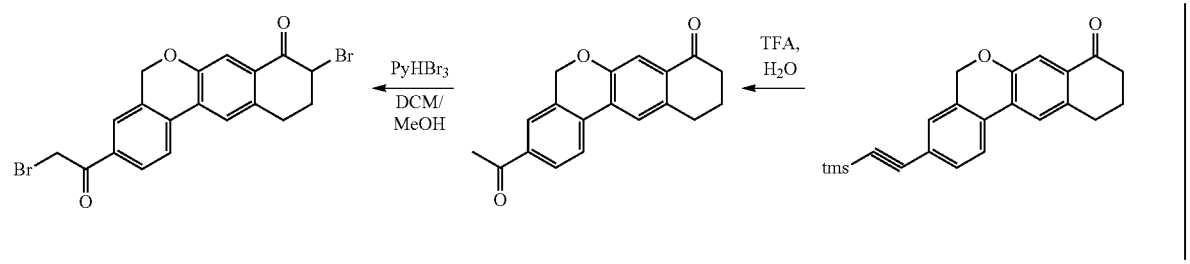

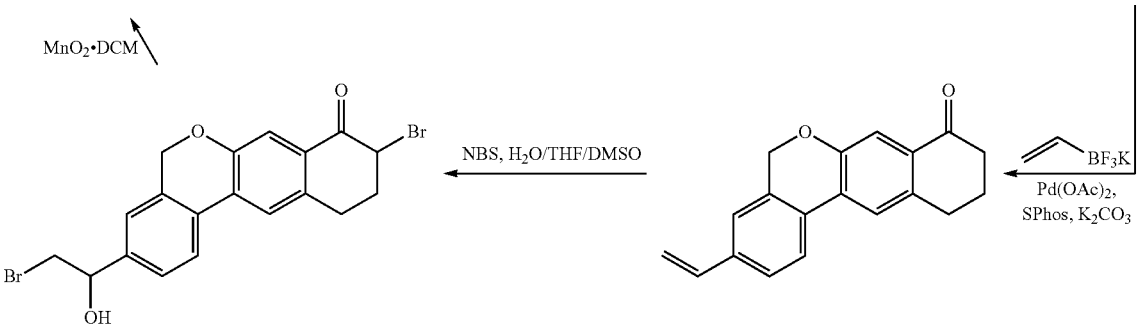

PCT publication No. 2015/191437 ("the '437 publication") discloses a process for preparation of compound of Formula I. The processes disclosed in the '437 publication is schematically represented as follows:
Scheme-2
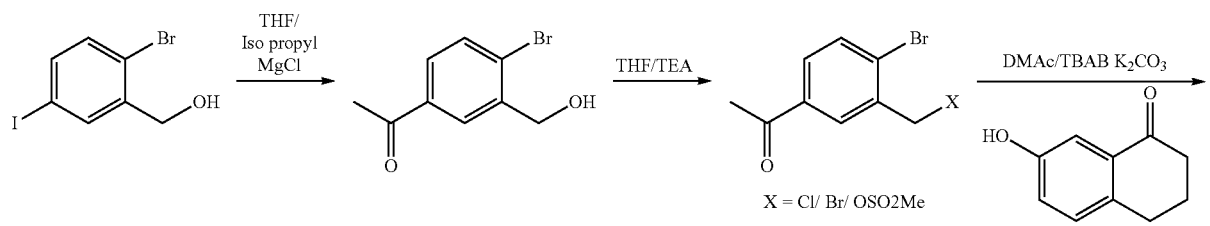
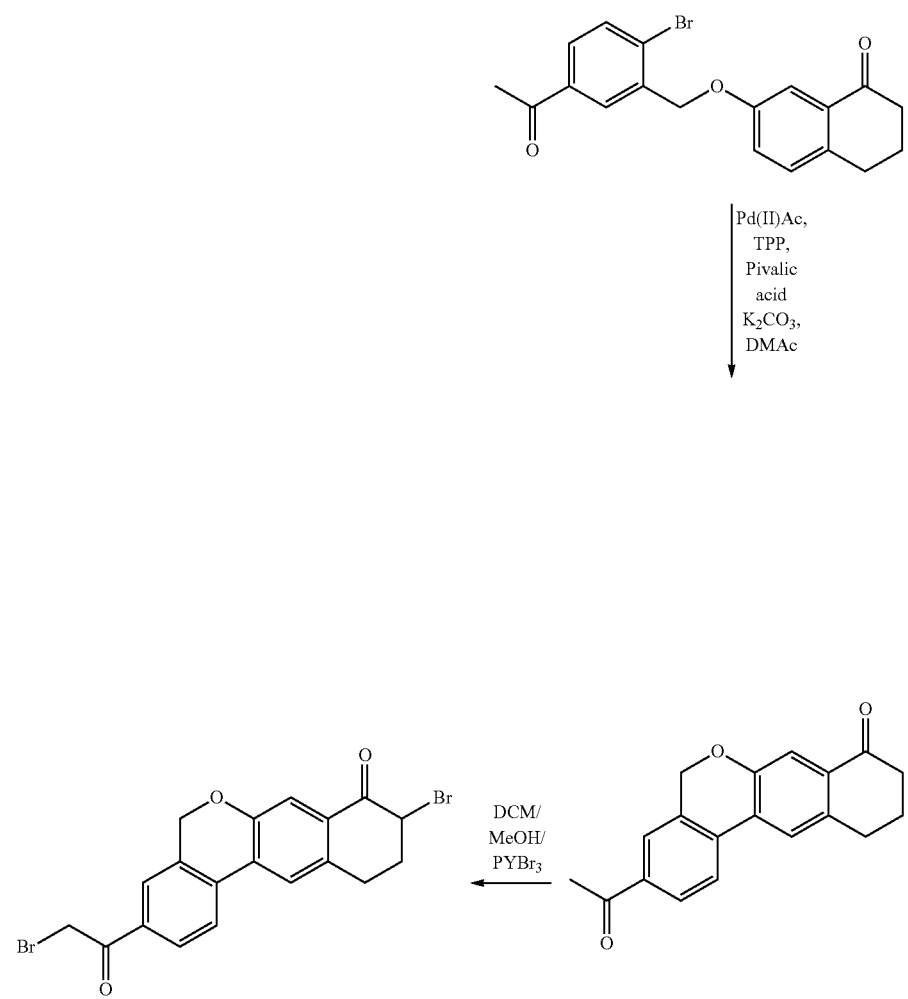

Scheme-3

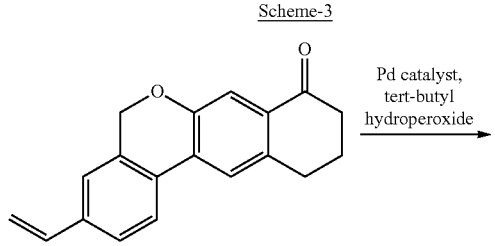

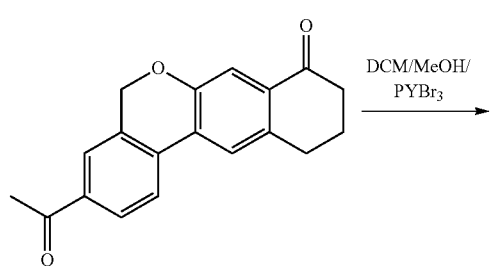

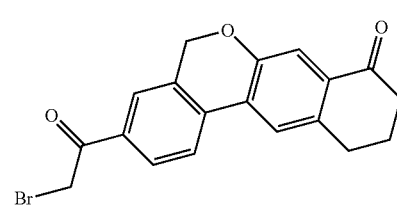

Scheme-4

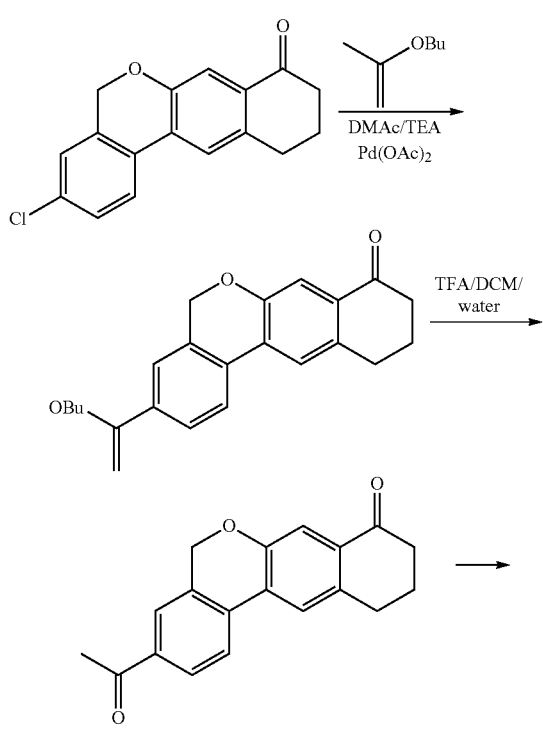

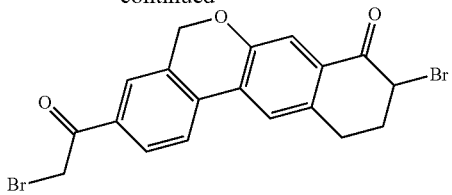

The above described processes have certain disadvantages as they involve usage of expensive starting materials and multiple palladium catalyzed reactions, which are not viable on cost effective commercial scale operations.

Hence, there is a need in the art to provide a process for the preparation of intermediates useful in the preparation of HCV Inhibitors, which does not rely on usage of expensive starting materials and other difficulties, and is readily amenable to commercial scale operations.

Among other aspects of the present invention, the present invention simplifies the process for the preparation of compound of Formula I with greater yield and high purity by using novel intermediates of Formula IV, IVa, and V.

SUMMARY OF THE INVENTION

In accordance with one embodiment, the present invention provides a process for the preparation of a compound of Formula I, wherein 'X' represents a halogen:

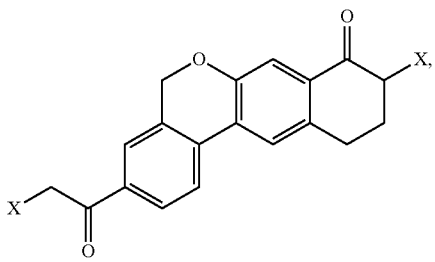

Formula I comprising:
a) reacting a compound of Formula II with a compound of Formula III to obtain a compound of Formula IV, wherein 'X' represents a halogen,

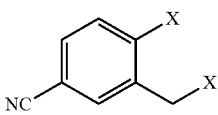

Formula II

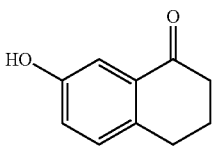

Formula III

-continued

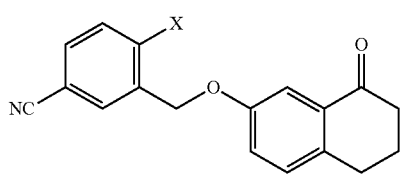
Formula IV b) cyclizing the compound of Formula IV to obtain a compound of Formula V,

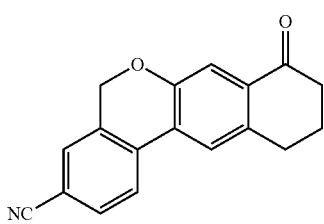
Formula V c) converting the compound of Formula V into a compound of Formula VI, and

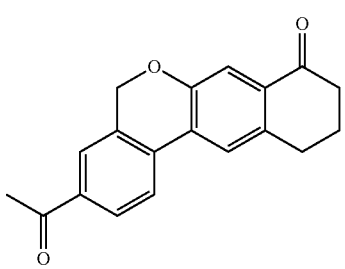
Formula VI d) converting the compound of Formula VI into the compound of Formula I.

In accordance with another embodiment, the present invention provides a process for the preparation of a compound of Formula I, wherein 'X' represents a halogen, comprising:

a) reacting a compound of Formula II with a compound of Formula III to obtain a compound of Formula IV, wherein 'X' represents a halogen, b) cyclizing the compound of Formula IV to obtain a compound of Formula V, and c) converting the compound of Formula V into the compound of Formula I.

In accordance with another embodiment, the present invention provides a process for the preparation of a compound of Formula I, wherein 'X' represents a halogen, comprising:

a) reacting a compound of Formula II with a compound of Formula III to obtain a compound of Formula IV, wherein 'X' represents a halogen, and b) converting the compound of Formula IV into the compound of Formula I.

In accordance with another embodiment, the present invention provides a process for the preparation of a compound of Formula Ia:

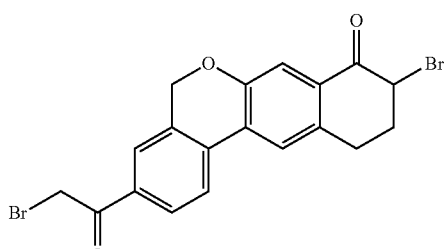
Formula Ia comprising:

a) reacting a compound of Formula IIa with a compound of Formula III to obtain a compound of Formula IVa,

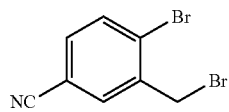
Formula IIa

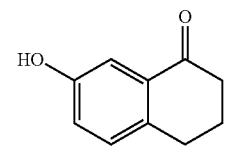
Formula III

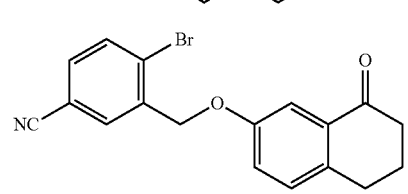
Formula IVa b) cyclizing the compound of Formula IVa to obtain a compound of Formula V,

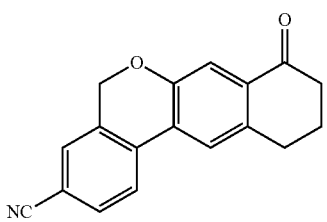
Formula V c) converting the compound of Formula V into a compound of Formula VI, and

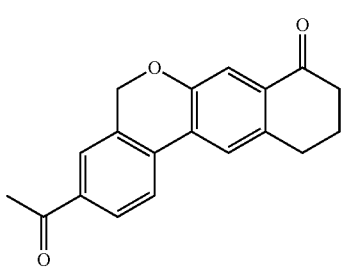
Formula VI d) converting the compound of Formula VI into the compound of Formula I.

In accordance with another embodiment, the present invention provides a compound of Formula IV, wherein 'X' represents a halogen, Formula IV

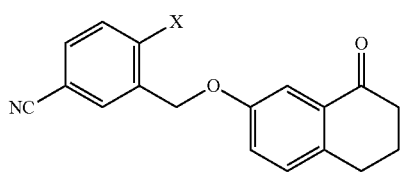

In accordance with another embodiment, the present invention provides a compound of Formula IVa, Formula IVa

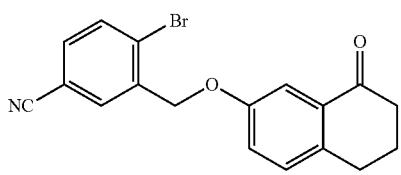

In accordance with another embodiment, the present invention provides a compound of Formula V, Formula V

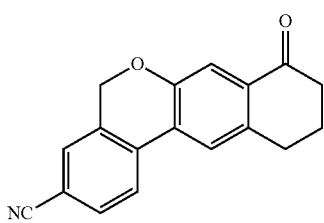

In accordance with another embodiment, the present invention provides a process for the preparation of Velpatasvir of Formula A, comprising preparing the 9-halo-3-(2-haloacetyl)-10,11-dihydro-5H-dibenzo[c,g]chromen-8(9H)-one of Formula I as per the process described above, and converting the 9-halo-3-(2-haloacetyl)-10,11-dihydro-5H-dibenzo[c,g]chromen-8(9H)-one of Formula I into the Velpatasvir of Formula A.

In accordance with another embodiment, the present invention provides a pharmaceutical composition useful in inhibiting HCV, comprising Velpatasvir of Formula A, prepared by the processes of the present invention and at least one pharmaceutically acceptable excipient.

DETAILED DESCRIPTION OF THE INVENTION

The present invention provides a process for the preparation of a compound of Formula I using novel intermediates. Further, the present invention involves converting the compound of Formula I into Velpatasvir of Formula A.

In accordance with one embodiment, the present invention provides a process for the preparation of the compound of Formula I, wherein 'X' represents a halogen:

Formula I

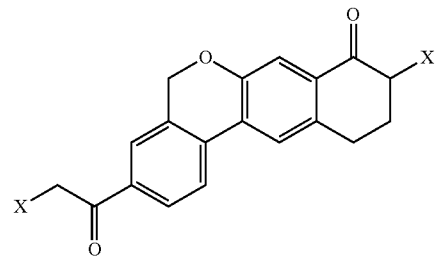

comprising:
a) reacting a compound of Formula II with a compound of Formula III to obtain a compound of Formula IV, wherein 'X' represents a halogen, Formula II

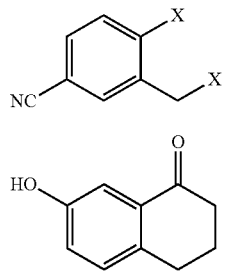

Formula III

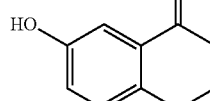

Formula IV

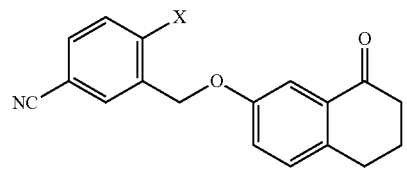

b) cyclizing the compound of Formula IV to obtain a compound of Formula V,

Formula V

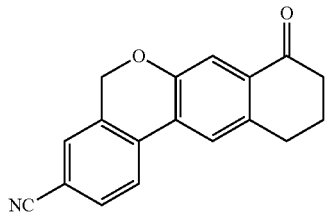

c) converting the compound of Formula V into a compound of Formula VI, and

Formula VI

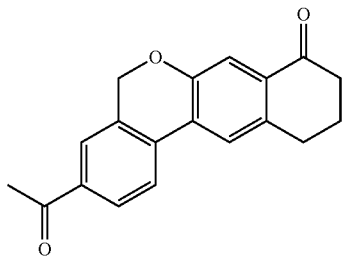

d) converting the compound of Formula VI into the compound of Formula I.

The starting material of compound of Formula II and Formula III are known in the art, and can be prepared by any known method. For example, the compound of Formula II may be synthesized as disclosed in U.S. Pat. No. 6,387,926, or may be by the process described in the present application. The compound of Formula III may be synthesized as disclosed in the Journal of Medicinal Chemistry, 1998, vol. 41, #7, pages 1068-1083.

Unless otherwise specified, the term 'X' represents a halogen, which is selected from one of fluoro (Fl), chloro (Cl), bromo (Br), and iodo (I).

In a preferred embodiment, the compound of Formula II and Formula IV can be represented as follows:

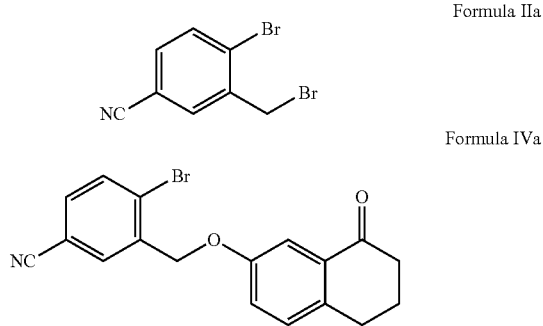

Formula IIa

Formula IVa

The starting compound of Formula IIa of the present invention may be prepared from 4-bromo-3-methylbenzonitrile by bromination as described in the following process.

In another embodiment, the present invention provides a process for the preparation of a compound of Formula IIa, comprising: brominating 4-bromo-3-methylbenzonitrile in the presence of 1,3-dibromo-5,5-dimethylhydantoin (DB-DMH) and optionally in the presence of a catalyst in a suitable solvent to obtain the compound of Formula IIa.

Exemplary catalysts used herein for the step of bromination include, but are not limited to, 2,2'-azobis(2-methylpropionitrile) (AIBN), 1,1'-azobis (cyclohexane carbonitrile) (ACCN), 4,4'-azobis(4-cyanovaleric acid), 4,4'-azobis(4-cyanovaleric acid), 1,1'-azobis(cyclohexanecarbonitrile), 2,2'-azobis(2-methylpropionamidine) dihydrochloride, ammonium persulfate, tert-butyl hydroperoxide, manganese dioxide, aluminium chloride, and the like, and mixtures thereof.

Suitable solvents for bromination include, but are not limited to, amides, nitriles, ethers, halogenated hydrocarbons, and mixtures thereof. The suitable amides include, but are not limited to, dimethyl formamide, dimethyl acetamide, N-methyl pyrrolidinone, and the like, and mixtures thereof. The suitable nitriles include, but are not limited to, acetonitrile, propionitrile, benzonitrile, and the like, and mixtures thereof. The suitable ethers include, but are not limited to, tetrahydrofuran, dimethyl ether, diisopropyl ether, methyl tertiary butyl ether, 1,4-dioxane, and the like, and mixtures thereof. The suitable halogenated hydrocarbons include, but are not limited to, methylene chloride, ethylene chloride, chloroform, and the like, and mixtures thereof.

The bromination reaction is advantageously carried out at a temperature of about 0° C. to reflux temperature, preferably at or below 85° C.

The resultant compound of Formula IIa can be further processed directly without isolating from the reaction solution.

Alternatively, the compound of Formula IIa may be isolated as a solid and used for a subsequent reaction. The isolation step includes washing the organic layer with an aqueous base solution followed by the organic layer being concentrated under vacuum to obtain the residue by any method known in the art, at the end of the reaction. For example, distillation, evaporation, rotational drying (such as with the Buchi Rotavapor), flash drying, spin flash drying, and the like, preferably distillation under vacuum. The resultant residue may be crystallized or slurried using a suitable organic solvent, for example a mixture of an ether solvent and a cyclic hydrocarbon solvent; preferably from a mixture of tertiary butyl methyl ether and heptane.

The step a) of the aforementioned process involves reaction of the compound of Formula II, preferably the compound of Formula IIa, with the compound of Formula III, to obtain a compound of Formula IV, preferably a compound of Formula IVa, in the presence of a suitable base and in a suitable solvent.

Exemplary suitable bases used herein for the step of reaction of the compound of Formula IIa with the compound of Formula III, include, but are not limited to, sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, triethylamine, diisopropyl ethylamine, N-methyl morpholine, pyridine, and the like, and mixtures thereof.

Suitable solvents for reaction of the compound of Formula IIa with the compound of Formula III include, but are not limited to, amides, nitriles, ethers, aromatic hydrocarbons, and mixtures thereof. The suitable amides include, but are not limited to, dimethyl formamide, dimethyl acetamide, N-methyl pyrrolidinone, and the like, and mixtures thereof. The suitable nitriles include, but are not limited to, acetonitrile, propionitrile, and the like, and mixtures thereof. The suitable ethers include, but are not limited to, tetrahydrofuran, 2-methyl tetrahydrofuran, methyl tertiary butyl ether, 1,4-dioxane, and the like, and mixtures thereof. The suitable aromatic hydrocarbons include, but are not limited to, toluene, xylene, and the like, and mixtures thereof.

The reaction of the compound of Formula IIa with the compound of Formula III is preferably carried out at a temperature of about 25° C. to reflux temperature.

The step b) of the aforementioned process involves cyclization of the compound of Formula IV, preferably of the compound of Formula IVa, to obtain the compound of Formula V in the presence of a suitable palladium catalyst, a suitable base, and in a suitable solvent at a temperature preferably of about 25° C. to reflux temperature.

The suitable palladium catalyst used herein is selected from the group consisting of tetrakis (triphenylphosphine) palladium(0), tetrakis(tri(otolyl) phosphine) palladium(0), Pd$_2$(dba)$_3$, [1,1'Bis(diphenylphosphino)ferrocene]dichloropalladium(II) (Pd(dppf)$_2$Cl$_2$), Palladium(II)acetate, and the like, and mixtures thereof.

Suitable bases used herein for cyclization of the compound of Formula IVa, include but are not limited to, alkali metal hydroxides such as lithium hydroxide, sodium hydroxide, potassium hydroxide, and the like, and mixtures thereof; alkali metal alkoxides such as sodium methoxide, sodium ethoxide, sodium tert-butoxide, potassium tert-butoxide, and the like, and mixtures thereof; alkali metal carbonates such as sodium carbonate, potassium carbonate, cesium carbonate, and the like, and mixtures thereof; alkali metal bicarbonates such as sodium bicarbonate, potassium bicarbonate, and the like, and mixtures thereof; and organic bases such as triethylamine, diisopropyl ethylamine, N-methyl morpholine, pyridine, and the like, and mixtures thereof.

Suitable solvents for cyclization of the compound of Formula IVa, include but are not limited to, ethers, amides, aromatic hydrocarbons, water, and mixtures thereof. The suitable ethers include, but are not limited to, tetrahydrofuran, dimethyl ether, diethyl ether, diisopropyl ether, methyl tertiary butyl ether, 1,4-dioxane, 1,2-dimethoxy ethane, and the like, and mixtures thereof. The suitable amides include, but are not limited to, dimethyl formamide, dimethyl acetamide, dimethyl sulfoxide, N-methyl pyrrolidinone, and the like, and mixtures thereof. The suitable aromatic hydrocarbons include, but are not limited to, toluene, xylene; and the like, and mixtures thereof.

The step c) of the aforementioned process involves converting the compound of Formula V into the compound of Formula VI in the presence of methyl magnesium halide, particularly methyl magnesium bromide in a suitable solvent.

Suitable solvents used for step c), include, but are not limit to, ethers such as tetrahydrofuran, dimethyl ether, diethyl ether, diisopropyl ether, methyl tertiary butyl ether, 1,4-dioxane, 1,2-dimethoxy ethane, and the like, and mixtures thereof.

The step c) is preferably carried out at a temperature of about 0° C. to reflux temperature.

The step c) optionally involves protecting the keto group in the compound of Formula V and then reacting with methyl magnesium halide, and then followed by in-situ deprotection of the protecting group to obtain the compound of Formula VI.

The protection of the keto group in the compound of Formula V is preferably carried out at a temperature of about 0° C. to reflux temperature.

The suitable keto protecting group used herein is selected from dimethyl acetals, diethyl acetals, 1,3-dioxanes, 1,3-dioxolanes, 1,3-dithianes, 1,3-dithiolanes, trimethyl silyl, triethyl silyl, and the like.

The protection of the keto group in the compound of Formula V may be carried out in the presence of a suitable base, which includes, but is not limited to, lithium bis(trimethylsilyl)amide, lithium diisopropylamide, lithium tetramethylpiperidide, sodium bis(trimethylsilyl)amide, potassium bis(trimethylsilyl)amide, sodium hydride, potassium hydride, and the like, and mixtures thereof.

The deprotection of the keto group may be carried out in the presence of a suitable deprotecting agent. The suitable deprotecting agent includes, but is not limited to, acids such as hydrochloric acid, sulfuric acid, p-toluenesulfonic acid, pyridinium p-toluenesulfonate, and the like, and mixtures thereof.

The step d) of the aforementioned process involves converting the compound of Formula VI into the compound of Formula I by any process known in the art, for example the processes shown in the aforementioned '718 patent and '437 PCT application.

In another embodiment, the present invention provides a compound of Formula IV, wherein 'X' represents a halogen,

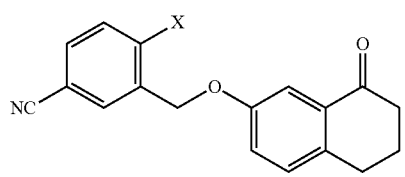

Formula IV

In another embodiment, the present invention provides a compound of Formula IVa,

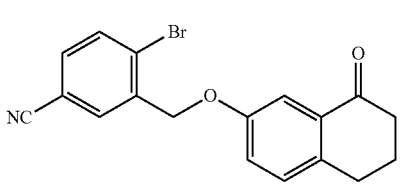

Formula IVa

In another embodiment, the present invention provides a compound of Formula V,

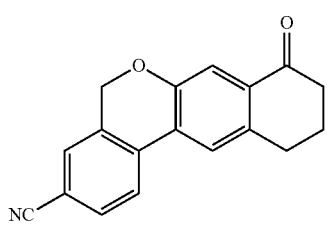

Formula V

In another embodiment, the present invention provides a process for the preparation of Velpatasvir, comprising: preparing the 9-halo-3-(2-haloacetyl)-10,11-dihydro-5H-dibenzo[c,g]chromen-8(9H)-one of Formula I as described above, and converting the 9-halo-3-(2-haloacetyl)-10,11-dihydro-5H-dibenzo[c,g]chromen-8(9H)-one into Velpatasvir by any process known in the art, for example the processes shown in the aforementioned '718 patent and '437 PCT application.

In another embodiment, the present invention provides a pharmaceutical composition, comprising Velpatasvir of Formula A prepared by the processes of the present invention and at least one pharmaceutically acceptable excipient.

EXAMPLES

The present invention will now be further explained in the following examples describing in detail processes that may be used in the preparation of the compounds described above. However, the present invention should not be construed as limited to the exemplified processes and preparations. One of ordinary skill in the art will understand how to vary the exemplified processes and preparations to obtain the desired results.

Example 1

Preparation of 4-bromo-3-(bromomethyl)-benzonitrile 4-bromo-3-methylbenzonitrile (80 g), 1,3-dibromo-5,5-dimethylhydantoin (70 g), azobisisobutyronitrile (6.7 g), and ethylene chloride (650 mL) were combined in a 1-L reaction flask. Then the reaction mixture was heated to 80-85° C. and stirred for 19 hr at the same temperature. The reaction mixture was allowed to cool to 20-25° C. and washed with saturated aqueous sodium bicarbonate solution (650 mL) followed by water (650 mL). The organic layer was separated and concentrated to a dark brown oil, which solidified upon standing. The resulting solid was stirred in a mixture of methyl tert-butyl ether (40 mL) and heptane (80 mL) for 3 hr. The resulting slurry was filtered and the filter cake was washed with heptane (80 mL). The filter cake was dried in a vacuum oven at 35° C. to obtain the title compound. Yield: 51.3 g; HPLC purity: 95.1%; $^1$H NMR (300 MHz, CDCl$_3$) δ 7.73 (d, 1H, J=2.0 Hz), 7.70 (d, 1H, J=8.3 Hz), 7.42 (dd, 1H, J=8.3, 2.0 Hz), 4.56 (s, 2H).

Example 2

Preparation of 4-bromo-3-(bromomethyl)-benzonitrile 4-bromo-3-methylbenzonitrile (9.8 g), 1,3-dibromo-5,5-dimethylhydantoin (7 g), and 1,2-dichloroethane (80 mL) were combined in a 1-L reaction flask and stirred under nitrogen at 10-15° C. To the reaction mass 2,2'-azobis (2-methypropionitrile) (0.82 g) was added and the reaction mixture was heated to 80-85° C. After completion of the reaction, the reaction mixture was filtered to remove 5,5-dimethylhydantoin (4.2 g). The mother liquor was used in the next step without further purification (Yield: 12 g wt/wt assay).

Example 3

Preparation of 7-(2-bromo-5-cyanobenzyloxy)-3,4-dihydronaphthalen-1(2H)-one 7-hydroxy-1-tetralone (26 g) and potassium carbonate (44 g) in N,N-dimethylacetamide (130 mL) were combined in a 1-L reaction flask. To the reaction mass a dimethylacetamide solution of 4-bromo-3-(bromomethyl)benzonitrile (44 g in 130 mL) was added at 25-30° C. The resultant reaction mixture was stirred at ambient temperature for 68 hr. To the reaction mixture water (520 mL) was added at 8-12° C. over 25 min and stirred for 30 min at 10° C. The precipitated solid was filtered, and to the solid, water (300 mL) was added and stirred for 45 min. The solid was filtered and washed with water (50 mL) and dried at 35° C. under vacuum for about 24 hr to obtain the title compound. Yield: 58.7 g; HPLC purity: 98.2%; $^1$H NMR (300 MHz, CDCl$_3$) δ 7.85 (m, 1H), 7.71 (d, 1H, J=8.2 Hz), 7.58 (d, 1H, J=2.7 Hz), 7.46 (dd, 11H, J=8.2, 2.0 Hz), 7.23 (d, 1H, J=10.4 Hz), 7.16 (dd, 11H, J=8.4, 2.7 Hz), 5.13 (s, 2H), 2.93 (dd, 1H, J=6.0, 6.0 Hz), 2.65 (dd, 1H, J=6.5, 6.5 Hz), 2.13 (pent., 2H, J=6.3 Hz).

Example 4

Preparation of 7-(2-bromo-5-cyanobenzyloxy)-3,4-dihydronaphthalen-1(2H)-one 7-hydroxy-1-tetralone (29.5 g) and potassium carbonate (50 g) in N,N-dimethylacetamide (150 mL) were combined in a 1-L reaction flask. To the reaction mass a dimethylacetamide solution of 4-bromo-3-(bromomethyl)benzonitrile (50 g in 160 mL) was added) at 20-25° C. over 43 min. The reaction mixture was stirred at 20° C. for 21 hr. After completion of the reaction, to the reaction mass water (620 mL) was added at 12° C. and the mixture was stirred at 12-15° C. for 30 min. The precipitated solid was collected by filtration and washed with water (3×30 mL) and dried under vacuum at 30° C. Then the solid was stirred in heptane (780 mL) at 25° C. for 5 hr, and filtered, washed with heptane (3×50 mL), and air dried for 3 days. The heptane slurry was repeated (1×620 mL and 1×540 mL) and dried to obtain the title compound. Yield: 51.8 g; HPLC purity: 93%.

The above solid was dissolved in isopropyl acetate (600 mL) at 80-85° C. and the reaction mass temperature was allowed to cool to 25-30°. The precipitated solid was filtered and washed with isopropyl acetate (35 mL) and dried under vacuum at 40° C. for 3 hr to obtain the title compound. Yield: 40.9 g; HPLC purity: 97.9%.

Example 5

Preparation of 3-cyano-10,11-dihydro-5H-dibenzo [c,g]chromen-8(9H)-one 7-(2-bromo-5-cyanobenzyloxy)-3,4-dihydronaphthalen-1 (2H)-one (1.32 kg), potassium carbonate (1.02 kg), pivalic acid (113.5 g), PPh$_3$ (29.1 g) and N,N-dimethylacetamide (6.6 lit) were combined in a 20-L reaction flask. Pd(OAc)$_2$ (24.9 g) was added to the reaction mass and then the reaction mixture was heated to 115-120° C. and stirred for 1.5 hr at the same temperature. After completion of the reaction, the reaction mass was allowed to cool to 10° C. and a mixture of methylene chloride (39.6 lit) and water (13.2 lit) was added. The organic and aqueous layers were separated, and the aqueous layer was extracted with methylene chloride (6.6 lit). The combined organic layer was washed with 20% sodium chloride solution (6.6 lit) and then filtered. The obtained filtrate was distilled off under vacuum to obtain the title compound.

Example 6

Preparation of 3-acetyl-10,11-dihydro-5H-dibenzo [c,g]chromen-8(9)-one 3-cyano-10,11-dihydro-5H-dibenzo[c,g]chromen-8(9H)-one (50 g), copper(I) bromide (2.61 g) and tetrahydrofuran (500 mL) were combined in a 1-L reaction flask and allowed to cool to 0° C. and stirred for 30 min at same temperature. To the reaction mass 1.0 M lithium bis(trimethylsilyl)amide in tetrahydrofuran (200 mL) was added at 0° C. and the reaction mass heated to 20° C. and stirred for 20 min at same temperature. To the reaction mass chlorotrimethylsilane (25.4 mL) was added at 15° C. and stirred for 10 min at 20° C. followed by 3.4 M methylmagnesium bromide in 2-methyltetrahydrofuran (160 mL) which was added over 1 hour at 15° C. and stirred for 16 hours at 20° C. Then the reaction mass was added slowly to the pre-cooled 2 M aqueous hydrochloric acid (500 mL) at below 20° C. and stirred for 5 hours at same temperature. Then the precipitated solid was filtered and washed with water (100 mL) and methanol (100 mL) and dried to obtain the title compound.

The filtrate was taken into a reaction flask and allowed to cool −20° C. and stirred for 18 hours at same temperature and the precipitated solid was filtered and washed with methanol (20 mL) and dried the wet compound to obtain the title compound. Yield: 41.8 g; HPLC purity: 98.5%.

Example 7

Preparation of 9-bromo-3-(2-bromoacetyl)-10,11-dihydro-5H-dibenzo[c,g]chromen-8(9)-one 3-acetyl-10,11-dihydro-5H-dibenzo[c,g]chromen-8(9)-one (5 g) was dissolved in a 9:1 mixture of methylene chloride and methanol (35 mL) at 20° C. To the reaction mass a methylene chloride solution of pyridinium tribromide was added drop wise at 20° C. and the reaction mass was stirred for 30 min at 25° C. After completion of the reaction, the precipitated solid was filtered and washed with methanol (2×25 mL) to obtain the title compound. Yield: 6.1 g; HPLC purity: 98%.

It will be understood that various modifications may be made to the reactions and preparations disclosed herein. Therefore, the above description should not be construed as exemplifications of various aspects of the present invention. The functions described above are for illustration purposes. Other arrangements and methods may be implemented by those skilled in the art without departing from the scope and spirit of the invention. Moreover, those skilled in the art will envision other modifications within the scope and spirit of the invention.

We claim:

1. A process for the preparation of a compound of Formula I comprising:
   a) reacting a compound of Formula II with a compound of Formula III to obtain a compound of Formula IV, where the compound of Formula II is,

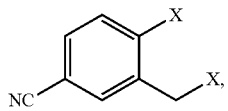
(Formula II)

wherein the compound of Formula III is,

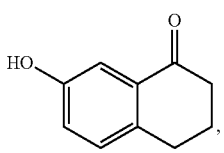
(Formula III)

wherein the compound of Formula IV is,

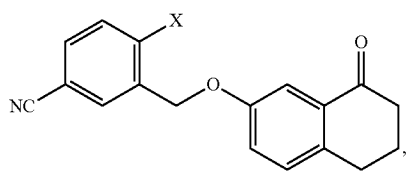
(Formula IV)

wherein 'X' represents a halogen;

b) converting the compound of Formula VI into the compound of Formula I, wherein the compound of Formula I is

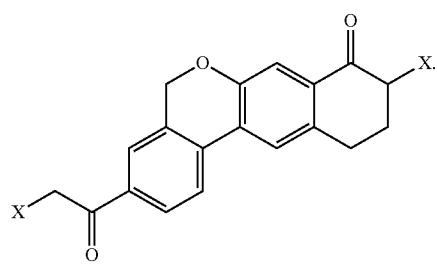
(Formula I)

2. A process for the preparation of a compound of Formula I comprising:
   a) reacting a compound of Formula II with a compound of Formula III to obtain a compound of Formula IV, where the compound of Formula II is,

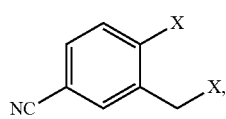
(Formula II)

wherein the compound of Formula III is,

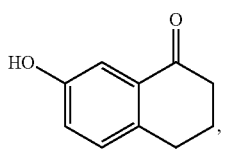
(Formula III)

wherein the compound of Formula IV is,

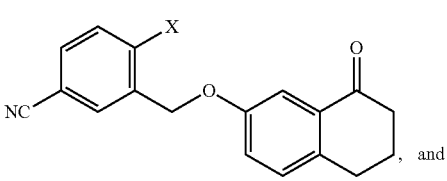
(Formula IV)

wherein 'X' represents a halogen;
   b) cyclizing the compound of Formula IV to obtain a compound of Formula V, wherein the compound of Formula V is,

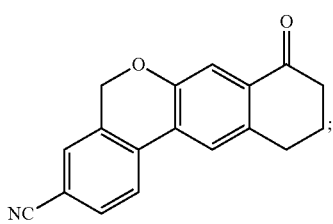
(Formula V)

c) converting the compound of Formula V into the compound of Formula I, wherein the compound of Formula I is

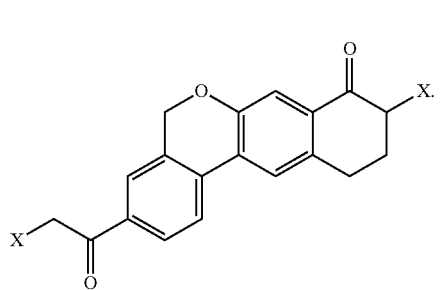
(Formula I)

3. A process for the preparation of a compound of Formula I comprising:
   a) reacting a compound of Formula II with a compound of Formula III to obtain a compound of Formula IV, where the compound of Formula II is,

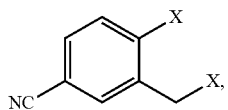
(Formula II)

wherein the compound of Formula III is,

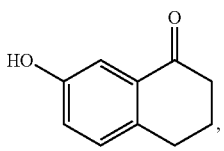
(Formula III)

wherein the compound of Formula IV is,

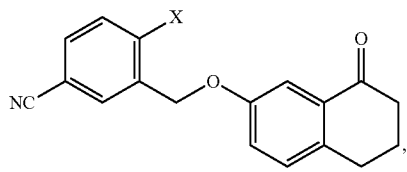
(Formula IV)

and
wherein 'X' represents a halogen;
   b) cyclizing the compound of Formula IV to obtain a compound of Formula V, wherein the compound of Formula V is,

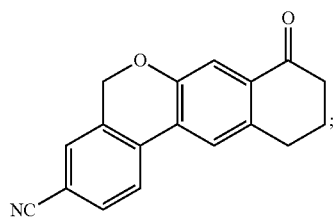
(Formula V)

c) converting the compound of Formula V into a compound of Formula VI, where the compound of Formula VI is,

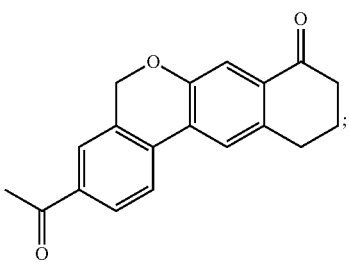
(Formula VI)

and
   d) converting the compound of Formula VI into the compound of Formula I, wherein the compound of Formula I is

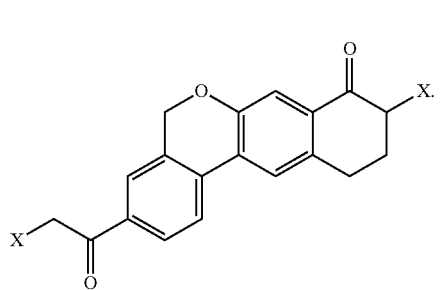
(Formula I)

4. The process according to claim 3, wherein the reacting step a) is performed in the presence of a base and a solvent.

5. The process according to claim 3, wherein the converting step c) is performed in the presence of methyl magnesium bromide and a solvent.

6. The process according to claim 3, wherein the converting step c) is performed in the presence of a solvent selected from one of tetrahydrofuran, dimethyl ether, diethyl ether, diisopropyl ether, methyl tertiary butyl ether, 1,4-dioxane, and 1,2-dimethoxy ethane, and mixtures thereof.

7. The process according to claim 3, wherein the converting step c) further comprises:
   protecting the keto group in the compound of Formula V with a protecting group;
   reacting the protected compound with methyl magnesium halide; and
   deprotecting in-situ the protecting group to obtain the compound of Formula VI.

8. The process according to claim 7, wherein the process of protecting the keto group in the compound of Formula V is preferably carried out at a temperature of about 0° C. to reflux temperature.

9. The process according to claim 7, wherein the keto protecting group is selected from one of a dimethyl acetal, a diethyl acetal, a 1,3-dioxane, a 1,3-dioxolane, a 1,3-dithiane, a 1,3-dithiolane, trimethyl silyl, and triethyl silyl.

10. The process according to claim 7, wherein the process of protecting the keto group in the compound of Formula V is carried out in the presence of a base selected from one of lithium bis(trimethylsilyl)amide, lithium diisopropylamide, lithium tetramethylpiperidide, sodium bis(trimethylsilyl) amide, potassium bis(trimethylsilyl)amide, sodium hydride, and potassium hydride, and mixtures thereof.

11. The process according to claim 7, wherein the process of deprotecting the keto group in the compound of Formula V is carried using a deprotecting agent selected from one of hydrochloric acid, sulfuric acid, p-toluenesulfonic acid, and pyridinium p-toluenesulfonate, and mixtures thereof.

12. The process according to claim 3, wherein the halogen 'X' is one of fluoro, chloro, bromo, and iodo.

13. The process according to claim 3, wherein the halogen 'X' is bromo, wherein the compound of Formula I is the compound of Formula Ia,

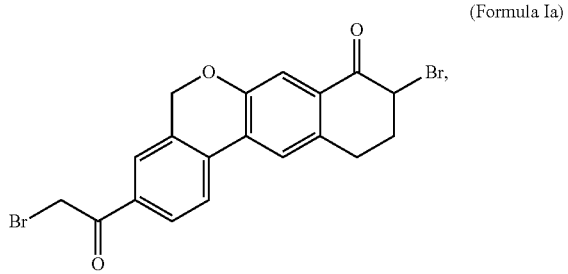 [SMILES: O=C(CBr)c1ccc2c(c1)COc1cc3c(cc1-2)CCC(Br)C3=O]

(Formula Ia)

wherein the compound of Formula II is the compound of Formula IIa,

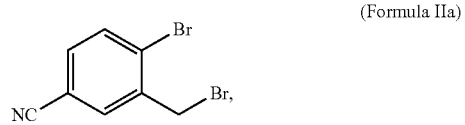 [SMILES: N#Cc1ccc(Br)c(CBr)c1]

(Formula IIa)

and
wherein the compound of Formula IV is the compound of Formula IVa,

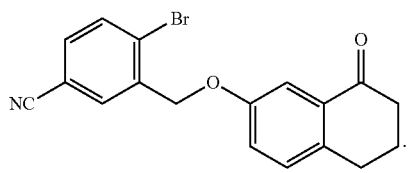

(Formula IVa)

14. The process according to claim 13, further comprising:
e) converting the compound of Formula Ia into the compound of Formula A, wherein the compound of Formula A is

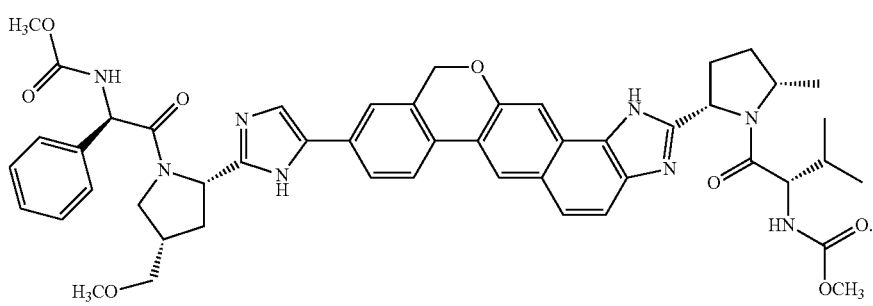

Formula A

15. The process according to claim 14, further comprising forming a pharmaceutical composition comprising the compound of Formula A and at least one pharmaceutically acceptable excipient.

16. The process according to claim 13, wherein the compound of Formula IIa is prepared by brominating 4-bromo-3-methylbenzonitrile in the presence of 1,3-dibromo-5,5-dimethylhydantoin (DBDMH), a solvent, and optionally in the presence of a catalyst.

17. The process according to claim 16, wherein when the catalyst is used, the catalysts is selected from one of 2,2'-azobis(2-methylpropionitrile), 1,1'-azobis (cyclohexane carbonitrile), 4,4'-azobis(4-cyanovaleric acid), 4,4'-azobis(4-cyanovaleric acid), 1,1'-azobis(cyclohexanecarbonitrile), 2,2'-azobis(2-methylpropionamidine) dihydrochloride, ammonium persulfate, tert-butyl hydroperoxide, manganese dioxide, and aluminium chloride, and mixtures thereof.

18. The process according to claim 16, wherein the solvent is selected from one of an amide, a nitrile, an ether, and a halogenated hydrocarbon, and mixtures thereof.

19. The process according to claim 18, wherein the amide is selected from one of dimethyl formamide, dimethyl acetamide, and N-methyl pyrrolidinone, and mixtures thereof; and wherein the nitrile is selected from one of acetonitrile, propionitrile, and benzonitrile, and mixtures thereof; and wherein the ether is selected from one of tetrahydrofuran, dimethyl ether, diisopropyl ether, methyl tertiary butyl ether, and 1,4-dioxane, and mixtures thereof; and wherein the halogenated hydrocarbon is selected from one of methylene chloride, ethylene chloride, and chloroform, mixtures thereof.

20. The process according to claim 16, wherein the compound of Formula IIa is used without isolating it from the bromination solution, or wherein the compound of Formula IIa is isolated from the bromination solution by washing the bromination solution with an aqueous base solution, concentrating the resulting solution under vacuum to obtain the solid compound, and optionally crystallizing the solid compound from an organic solvent selected from one of an ether solvent and a cyclic hydrocarbon solvent.

21. The process according to claim 13, wherein the reaction step a) is performed in an aqueous base selected from one of sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, triethylamine, diisopropyl ethylamine, N-methyl morpholine, and pyridine, and mixtures thereof.

22. The process according to claim 13, wherein the reaction step a) is performed in a solvent selected from one of an amide, a nitrile, an ether, and an aromatic hydrocarbons, and mixtures thereof.

23. The process according to claim 22, wherein the amide is selected from one of dimethyl formamide, dimethyl acetamide, and N-methyl pyrrolidinone, and mixtures thereof; and wherein the nitrile is selected from one of acetonitrile, and propionitrile, and mixtures thereof; and wherein the ether is selected from one of tetrahydrofuran, 2-methyl tetrahydrofuran, methyl tertiary butyl ether, and 1,4-dioxane, mixtures thereof; and wherein the aromatic hydrocarbon is selected from one of toluene, and xylene, and mixtures thereof.

24. The process according to claim 13, wherein the cyclization step b) is carried out in the presence of a palladium catalyst, a base, and a solvent.

25. The process according to claim 24, wherein the palladium catalyst is selected from the group consisting of tetrakis (triphenylphosphine) palladium(0), tetrakis(tri(otolyl) phosphine) palladium(0), $Pd_2(dba)_3$, [1,1'-bis(diphenylphosphino)ferrocene]dichloropalladium(II) $(Pd(dppf)_2Cl_2)$, and palladium(II)acetate, and mixtures thereof.

26. The process according to claim 24, wherein the base is selected from one of an alkali metal hydroxide, an alkali metal alkoxide, an alkali metal carbonate, an alkali metal bicarbonate, and an organic base, and mixtures thereof.

27. The process according to claim 24, wherein the solvent is selected from one of an ether, an amide, an aromatic hydrocarbon, and water, and mixtures thereof.

28. A process for the preparation of a compound of Formula Ia comprising:
a) reacting a compound of Formula IIa with a compound of Formula III to obtain a compound of Formula IVa, wherein the compound of Formula IIa is

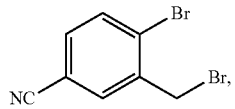

(Formula IIa)

wherein the compound of Formula III is

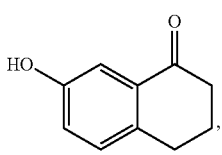

(Formula III)

and
wherein the compound of Formula IVa is

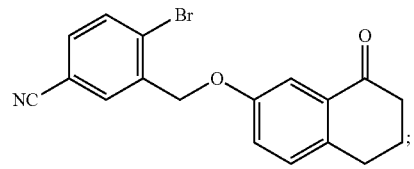

(Formula IVa)

b) cyclizing the compound of Formula IVa to obtain a compound of Formula V, wherein the compound of Formula V is

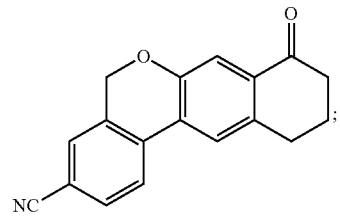

(Formula V)

c) converting the compound of Formula V into a compound of Formula VI, wherein the compound of Formula VI is

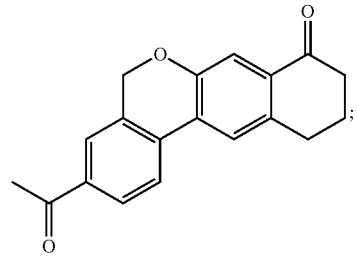

(Formula VI)

and
d) converting the compound of Formula VI into the compound of Formula Ia, wherein the compound of Formula Ia is

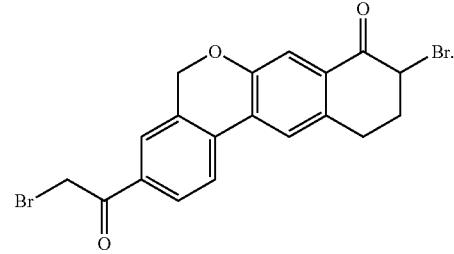

(Formula Ia)

29. The process according to claim 28, further comprising:
  e) converting the compound of Formula Ia into the compound of Formula A, wherein the compound of Formula A is

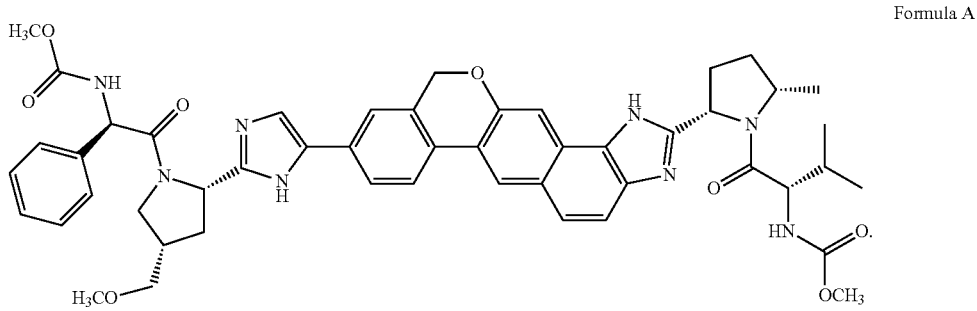 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

Formula A

30. The process according to claim 29, further comprising forming a pharmaceutical composition, the composition comprising the compound of formula A obtained in step e and at least one pharmaceutically acceptable excipient.

31. A compound of Formula IV, wherein 'X' represents a halogen, and wherein the compound of Formula IV is

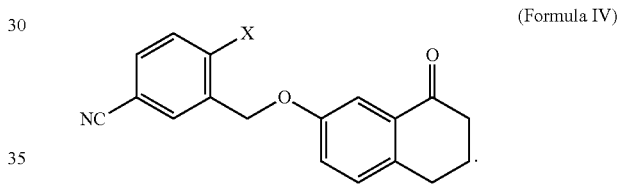

(Formula IV)

32. The compound according to claim 31, wherein the halogen 'X' is bromo.

* * * * *

UNITED STATES PATENT AND TRADEMARK OFFICE
CERTIFICATE OF CORRECTION

PATENT NO.      : 9,957,279 B2
APPLICATION NO. : 15/583722
DATED           : May 1, 2018
INVENTOR(S)     : Kirshna R. Yalamareddy et al.

Page 1 of 1

It is certified that error appears in the above-identified patent and that said Letters Patent is hereby corrected as shown below:

In the Claims

Claim 1, Column 20, Line 1, should read --IV-- not "VI"

Signed and Sealed this
Eighteenth Day of August, 2020

Andrei Iancu
*Director of the United States Patent and Trademark Office*